(12) United States Patent
Kumaoh et al.

(10) Patent No.: US 9,101,648 B2
(45) Date of Patent: Aug. 11, 2015

(54) PHARMACEUTICAL COMPOSITION COMPRISING MANNOOLIGOSACCHARIDES DERIVED FROM COFFEE FOR TREATMENT OF LIFESTYLE-RELATED DISEASE, AND FOOD USEFUL FOR TREATMENT OF LIFESTYLE-RELATED DISEASE

(75) Inventors: Toshio Kumaoh, Tokyo (JP); Kazuto Ozaki, Tokyo (JP); Ichiro Asano, Tokyo (JP); Shigeyoshi Fujii, Tokyo (JP); Naoto Imura, Tokyo (JP)

(73) Assignees: Intercontinental Great Brands LLC, East Hanover, NJ (US); Ajinomoto General Foods, Inc., Tokyo (JP)

( * ) Notice: Subject to any disclaimer, the term of this patent is extended or adjusted under 35 U.S.C. 154(b) by 0 days.

(21) Appl. No.: 13/260,405

(22) PCT Filed: Mar. 24, 2010

(86) PCT No.: PCT/JP2010/055078
§ 371 (c)(1),
(2), (4) Date: Dec. 8, 2011

(87) PCT Pub. No.: WO2010/110313
PCT Pub. Date: Sep. 30, 2010

(65) Prior Publication Data
US 2012/0101058 A1    Apr. 26, 2012

(30) Foreign Application Priority Data
Mar. 26, 2009  (WO) ............... PCT/JP2009/056115

(51) Int. Cl.
| A61K 31/715 | (2006.01) |
| A23L 1/09 | (2006.01) |
| A23L 1/30 | (2006.01) |
| A61K 31/702 | (2006.01) |
| A61K 36/74 | (2006.01) |
| A23F 5/00 | (2006.01) |

(52) U.S. Cl.
CPC ............... *A61K 31/715* (2013.01); *A23L 1/09* (2013.01); *A23L 1/30* (2013.01); *A61K 31/702* (2013.01); *A61K 36/74* (2013.01); *A23F 5/00* (2013.01); *A23V 2200/3202* (2013.01)

(58) Field of Classification Search
None
See application file for complete search history.

(56) References Cited

U.S. PATENT DOCUMENTS

| 6,576,275 | B1 | 6/2003 | Hoving et al. |
| 8,029,829 | B2 | 10/2011 | Okubo et al. |
| 2003/0162300 | A1 | 8/2003 | Kunz et al. |
| 2006/0286238 | A1 | 12/2006 | Zehentbauer et al. |
| 2007/0003678 | A1 | 1/2007 | Zehentbauer et al. |
| 2008/0213425 | A1* | 9/2008 | Asano et al. ............. 426/2 |
| 2009/0053381 | A1 | 2/2009 | Fukuda et al. |
| 2010/0048505 | A1 | 2/2010 | Fujii et al. |

FOREIGN PATENT DOCUMENTS

| EP | 0 008 398 B1 | 5/1982 |
| EP | 2 196 208 A1 | 6/2010 |
| JP | 62-111671 A | 5/1987 |
| JP | 2-200147 A | 8/1990 |
| JP | 9-002917 A | 1/1997 |
| JP | 9-143465 A | 6/1997 |
| JP | 9-221667 A | 8/1997 |
| JP | 2002-095450 A | 4/2002 |
| JP | 2002-262827 A | 9/2002 |
| JP | 2003-516757 A | 5/2003 |
| JP | 2003-310162 A | 11/2003 |
| JP | 2004-267177 A | 9/2004 |
| JP | 2005-124500 A | 5/2005 |
| JP | 2006-042624 A | 2/2006 |
| JP | 2006-83127 A | 3/2006 |
| JP | 2006-169135 A | 6/2006 |
| JP | 2006-193502 A | 7/2006 |
| JP | 2006-199706 A | 8/2006 |
| JP | 2006-306799 A | 11/2006 |
| JP | 2007-246443 A | 9/2007 |
| JP | 2006-169256 A | 2/2008 |
| JP | 2008-22778 A | 2/2008 |
| JP | 2008-503568 A | 2/2008 |
| JP | 2008-088187 A | 4/2008 |
| JP | 2009-165498 A | 7/2009 |
| WO | 2005/122790 A1 | 12/2005 |
| WO | 2006/064761 A1 | 6/2006 |
| WO | 2006/082643 A1 | 8/2006 |
| WO | WO 2008011562 A2 * | 1/2008 ......... A61K 31/7016 |

OTHER PUBLICATIONS

Asano, Hamaguchi, Juji and Iino. In Vitro Digestibility and Fermentation of Mannooligosaccharides from Coffee Mannan. Food Sci Technol Res, 9, 1, 2003, pp. 62-66.*

Simon, Complex carbohydrates in development as human pharmaceuticals. Exp Opin Invest Drugs, 3, 3, 1994, pp. 223-239.*

(Continued)

*Primary Examiner* — Shaojia Anna Jiang
*Assistant Examiner* — Dale R Miller
(74) *Attorney, Agent, or Firm* — Fitch, Even, Tabin & Flannery, LLP

(57) ABSTRACT

A pharmaceutical composition for preventing or treating lifestyle-related disease is provided. Also provided is a food useful for the prevention or treatment of lifestyle-related disease. The pharmaceutical composition contains, as an active ingredient, a sugar in which a mannose unit makes up 66% or more in terms of the number of mannose units and which has a polymerization degree of 3 to 10.

17 Claims, 2 Drawing Sheets

(56) References Cited

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002, retrieved on Mar. 24, 2011 form www.iime.org/glossary.htm.*

Yeh, Eisenberg, Kaptchuk and Phillips. Systematic review of herbs and dietary supplements for glycemic control in diabetes. Diabetes Care, 26, 4, 2003. pp. 1277-1294.*

"Lifestyle disease" in Medical Dictionary retrieved on Apr. 23, 2013 from http://www.medterms.com/script/main/art.asp?articlekey=38316.*

Mussato and Mancilha. Non digestible oligosaccharides: a review. Carb Poly, 68, 2007, pp. 587-597.*

Norden, Lundblad, Svensson, Ockerman and Autio. A mannose containing trisaccharide isolated from urines of three patients with mannosidosis. J. Biol Chem. 248, 17, 1973, pp. 6210-6215.*

Asano, I., Umemura, M., Fujii, S., Hoshino, H., & Iino, H. (2004). Effects of mannooligosaccharides from coffee mannan on fecal microflora and defecation in healthy volunteers. Food science and technology research, 10(1), 93-97.*

Cani, P. D., Neyrinck, A. M., Fava, F., Knauf, C., Burcelin, R. G., Tuohy, K. M., . . . & Delzenne, N. M. (2007). Selective increases of bifidobacteria in gut microflora improve high-fat-diet-induced diabetes in mice through a mechanism associated with endotoxaemia. Diabetologia, 50(11), 2374-2383.*

International Bureau of WIPO, English translation of the International Preliminary Report on Patentability for International Application PCT/JP2010/055078 dated Oct. 27, 2011 (8 pages).

Ichiro Asano et al., "Effects of 'Coffee Beverage' Containing Mannooligosaccharides from Coffee on Human Abdominal Fat by Long Term Ingestion," Japan Journal of Food Engineering, Jun. 15, 2003, vol. 6, No. 2, pp. 39-47, with English Abstract.

Shigeo Sakai, "Kinosei Shokuhin to Kenko Iji" Food Science, Apr. 10, 2008, vol. 50, No. 5, pp. 78-86, in Japanese, no English Abstract is available.

Hiroshi Mano et al., "Shiritakatta Shokuhin Seibun no Kino to Evidence Mannooligosaccharide," Shokuseikatsu, Nov. 1, 2008, vol. 102, No. 11, pp. 39-42, in Japanese, no English Abstract is available.

Toshio Kumano, "Coffee Mame Manno-Oligosaccharide no Kinosei," Japanese Council for Advanced Food Ingredients Research Koen Shiryo, Feb. 1, 2008, vol. 45, pp. 25-28, with English Summary.

European Patent Office Extended European Search Report dated Aug. 29, 2012 for European Application No. 10756209.4, 12 pages.

Tomohiro Tsuchiya et al., "Effects of Coffee Mannooligosaccharides on Adipocyte in High Fat Diet Fed Mice," Basic Pharmacology & Therapeutics, Nov. 20, 2007, vol. 35, No. 11, pp. 1107-1114, with English Abstract, XP009160850.

Toshio Kumao et al., "Effect of Coffee Drink Containing Mannooligosaccharides on Total Amount of Excreted Fat in Healthy Adults," Journal of Health Science, Jan. 1, 2006, vol. 52, No. 4, pp. 482-485, XP55035974.

Izumi Hoshino-Takao et al., "Effects of Mannooligosaccharides from Coffee Mannan on Blood Pressure in Dahl Salt-Sensitive Rats," Journal of Nutritional Science and Vitaminology, Apr. 1, 2008, vol. 54, No. 2, pp. 181-184, XP007910587.

Myriam Richelle et al., "Comparison of the Antioxidant Activity of Commonly Consumed Polyphenolic Beverages (Coffee, Cocoa, and Tea) Prepared per Cup Serving," J. Agric. Food Chem., 2001, vol. 49, pp. 3438-3442.

Mark F. McCarty, Nutraceutical resources for diabetes prevention—an update, Medical Hypotheses, 2005, vol. 64, pp. 151-158.

Sola Ogundipe, "If you must drink, drink coffee," Jan. 7, 2012 [online], [retrieved on Jul. 6, 2012]. Retrieved from the Internet: <URL: http://www.vanguardngr.com/2012/01/if-you-must-drink-drink-coffee/>, 3 pages.

European Patent Office Extended European Search Report dated Jul. 12, 2012 for European Patent Application No. 9842242.1, 9 pages.

European Patent Office Extended European Search Report dated Jul. 17, 2012 for European Patent Application No. 09842243.9, 9 pages.

International Bureau of WIPO, English translation of the International Preliminary Report on Patentability dated Oct. 27, 2011 for International Application PCT/JP2009/056118, 7 pages.

International Bureau of WIPO, English translation of the International Preliminary Report on Patentability dated Oct. 27, 2011 for International Application PCT/JP2009/056120, 7 pages.

T. Sakano et al., Machine English Translation of JP 2006-042624 A (originally published in Japanese Feb. 16, 2006), machine translation obtained on May 30, 2013, 11 pages.

* cited by examiner

PHARMACEUTICAL COMPOSITION COMPRISING MANNOOLIGOSACCHARIDES DERIVED FROM COFFEE FOR TREATMENT OF LIFESTYLE-RELATED DISEASE, AND FOOD USEFUL FOR TREATMENT OF LIFESTYLE-RELATED DISEASE

CROSS-REFERENCE TO RELATED APPLICATIONS

This application is a U.S. national phase application filed under 35 U.S.C. §371 of International Application PCT/JP2010/055078, filed on Mar. 24, 2010, designating the United States, which is hereby incorporated herein by reference in its entirety.

TECHNICAL FIELD

The present application relates to a pharmaceutical composition and a food product for preventing or treating lifestyle-related diseases containing mannooligosaccharides with a specific degree of polymerization.

BACKGROUND ART

Obesity has been on the rise year after year due to factors such as the consumption of a high-fat diet resulting from the westernization of dietary habits, lack of daily exercise, and overeating as a result of excessive stress. Obesity causes the accumulation of large quantities of lipids in the liver, which leads to lifestyle-related diseases such as diabetes, hypertension, hyperlipidemia, heart disease, and cerebral hemorrhage. Therefore, the prevention of obesity is an extremely important factor in the prevention of lifestyle-related diseases. In particular, as we now prepare for an aged society, increases in lifestyle-related diseases have become problematic, and means for preventing obesity have also attracted attention from the perspective of preventive medicine. Searches for substances involved in the prevention of obesity from various food products and research on the action of these substances are therefore under way, and mannooligosaccharides have been the focus of attention from among these substances.

Japanese Unexamined Patent Application Publication 2006-169256 discloses the fact that mannooligosaccharides have a serum lipid improving action. Japanese Unexamined Patent Application Publication 2008-022778 discloses the fact that mannooligosaccharides have a diabetes preventing action. Further, Japanese Unexamined Patent Application Publication 2006-083127 discloses the fact that mannooligosaccharides have effects that prevent lifestyle-related diseases caused by obesity such as a body lipid reducing action. The Japan Journal of Food Engineering (6(4), 301-304 (2005)) has reported that mannooligosaccharides have an action which inhibits the absorption of ingested lipids, and the Journal of Medicine and Pharmaceutical Science (54(4), 505-509 (2005)) has reported that mannooligosaccharides have an action which reduces liver lipids.

However, it was previously unknown that the degrees of these actions greatly fluctuate due to changes in the degree of polymerization of mannooligosaccharides.

SUMMARY

The present application is directed to a pharmaceutical composition for preventing or treating lifestyle-related diseases. The present application is also directed to providing a food product which is useful for preventing lifestyle-related diseases.

The present inventors carefully selected the sugar compositions of mannooligosaccharides reported previously and discovered that simple substances or mixtures formed with a degree of polymerization of 3-10 inhibit the uptake of lipids or sugars into the body and thereby powerfully reduce the lipids accumulated in the liver. The present inventors also discovered that such mixtures promote the growth of bifidobacteria.

The present application is concerned with a pharmaceutical composition for preventing or treating lifestyle-related diseases using, as an active ingredient, a sugar with a degree of polymerization of 3-10 and mannose units constituting at least 66% of the numerical content. The active ingredient is preferably a sugar with a degree of polymerization of 3-10 and mannose units constituting at least 90% of the numerical content, or more preferably at least 95% of the numerical content, and most preferably a sugar with a degree of polymerization of 3-10 comprised entirely of mannose units.

In one preferable mode, the sugar of the present invention is obtained by performing hydrolysis processing on a mannan, and this mannan is preferably obtained from coffee beans and/or a coffee extract residue.

In a preferable mode, the mannooligosaccharides of the present invention are β-1,4-mannooligosaccharides.

In a preferable mode, the lifestyle-related disease to be prevented or treated is caused by lipid absorption and/or sugar absorption, and it is particularly preferably caused by increases in liver lipids.

The present application is also concerned with a method for preventing or treating lifestyle-related diseases, wherein an effective dose of the pharmaceutical composition described above is administered to a patient who is at risk of contracting or is suffering from a lifestyle-related disease.

The present application is also concerned with the manufacture of a pharmaceutical composition for preventing or treating lifestyle-related diseases, wherein a sugar with a degree of polymerization of 3-10 and mannose units constituting at least 66% of the numerical content is used.

The present application is also concerned with a food product containing a sugar with a degree of polymerization of 3-10 and mannose units constituting at least 66% of the numerical content.

The pharmaceutical composition of the present application demonstrates a powerful lipid and/or sugar absorption inhibiting action and thereby reduces lipids accumulated in the liver. As a result, it exhibits an internal organ lipid reducing action, a serum lipid improving action, a blood sugar level reducing or increase-inhibiting action, and a blood pressure reducing or increase-inhibiting action, which makes it useful for the prevention or treatment of lifestyle-related diseases such as obesity, metabolic syndrome, hyperlipidemia, diabetes, myocardial infarction, arteriosclerosis, cerebral infarction, cerebral hemorrhage, angina pectoris, and hypercholesterolemia. Since the pharmaceutical composition of the present invention has a bifidobacteria growth promoting action, it is also useful for preventing or treating lifestyle-related diseases such as cancer by favorably maintaining the intestinal environment. In addition, the food product of the present invention, which can be ingested with daily meals, is useful for the prevention of lifestyle-related diseases.

DETAILED DESCRIPTION

Figure 1:
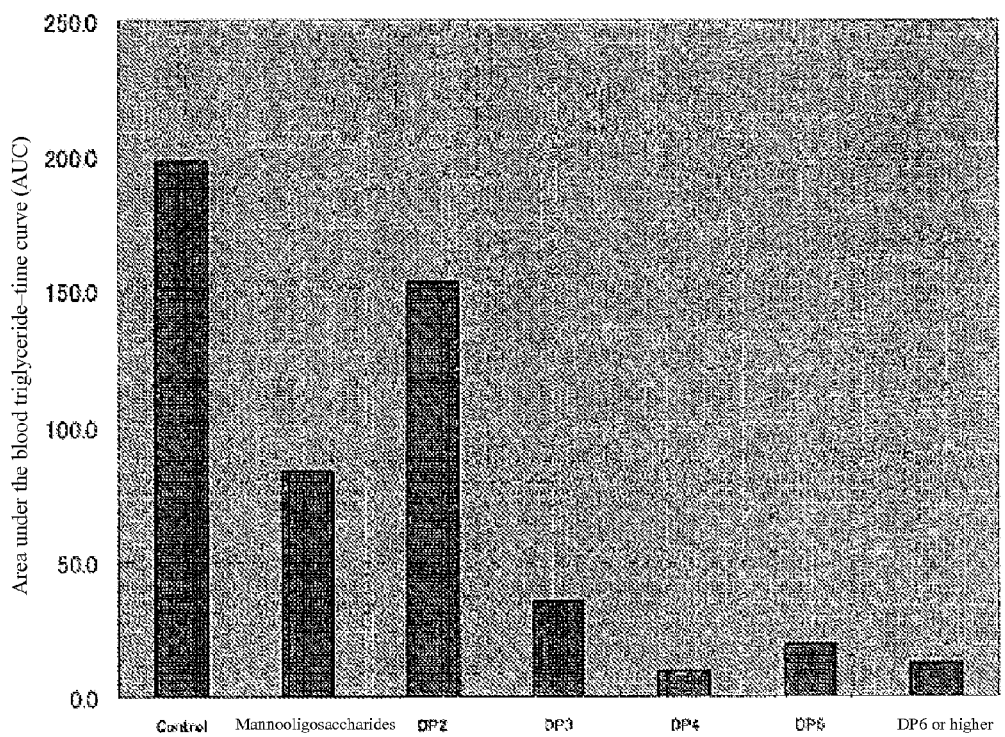
FIG. 1 shows the inhibition of lipid absorption due to the administration of fractions obtained in Embodiment 1.

In addition to mannose, the sugar with a degree of polymerization of 3-10 and mannose units constituting at least 66% of the numerical content in the present application also uses at least one type of monosaccharide such as glucose, fructose, or galactose as a constitutional unit.

Such a sugar is a fraction obtained by removing as much sugar with a degree of polymerization of 2 or less as possible from the hydrolysate of mannan, which contains oligosaccharides primarily consisting of mannose with a degree of polymerization of 1-10. The hydrolyzed mannan may be from any supply source. Examples include mannan, tsukuneimo mannan, or yamaimo mannan contained in coffee beans, coffee extract residues, copra meal obtained from coconut palms, or the South African Huacra Palm. Mannan obtained from coffee beans and/or coffee extract residues are particularly preferable.

This fraction ordinarily uses as its main ingredient a mixture of various simple substances of mannooligosaccharides with 3-10 mannose units—in other words, mannotriose, mannotetraose, mannopentaose, mannohexaose, mannoheptaose, mannooctaose, mannononaose, and mannodecaose—but it may also be further fractionated into each simple substance. The fraction of the present invention may contain a slight residual quantity of oligosaccharides with degrees of polymerization of 2 or less, but it is preferable for this quantity to be as small as possible, and a sugar with a degree of polymerization of 3-10 and mannose units constituting at least 90% of the numerical content is preferable. It is even more preferable for the sugar to contain at least 95% mannose units, and a sugar with a degree of polymerization of 3-10 consisting entirely of mannose units is most preferable.

The sugar with a degree of polymerization of 3-10 and mannose units constituting at least 66% of the numerical content in the present application can be preferably obtained by processing mannan contained in raw coffee beans, roasted coffee beans, or used coffee residues with one or more methods selected from acid hydrolysis, high-temperature thermal hydrolysis, oxygen hydrolysis, and microbial fermentation, purifying it with a method such as activated carbon treatment, absorbent resin treatment, ion-exchange resin treatment, or ion-exchange membrane treatment, separating it from the coffee residue, and then removing as much of the fractions with degrees of polymerization of 2 or less as possible by ion-exchange column chromatography or solvent treatment with ethanol or the like.

Examples of acids that may be used in acid hydrolysis include sulfuric acid and hydrochloric acid. The degree of acidity is pH 0-2. The temperature in high-temperature thermal hydrolysis is 190-250° C. Oxygen hydrolysis is performed by suspending mannan or the mannan supply source in an aqueous medium and then adding commercially available cellulase and hemicellulase, for example, and stirring. The concentration of the oxygen that is used is 0.01%-1%, and the temperature is 30-80° C. Examples of bacterial strains used in microbial fermentation include *Aspergillus niger*, *Bacillus subtilis*, and *Rhizopus oryzae*.

An example of a resin to be used in absorbent resin treatment is a styrene-divinylbenzene polymer. SK-1B is an example of an ion-exchange resin to be used in ion-exchange resin treatment.

Examples of fillers to be used in ion-exchange column chromatography, which is performed in order to remove as many fractions with degrees of polymerization of 2 or less as possible, include UBK-530 and UBK-510L. Fractions with even higher purity can be obtained by passing them several times through columns filled with each of the two types of ion-exchange resins and connected in series.

A reaction solution containing the fraction obtained with the method described above can be purified as necessary. Examples of purification methods include bone charcoal, activated charcoal, carbonate saturation, absorbent resins, magnesia method, decolorization and deodorization with a solvent extraction method or the like, ion-exchange resins, ion-exchange membranes, and desalination or deacidification with electrodialysis or the like. The purification conditions can be selected appropriately in accordance with the quantities of pigment, salt, and acid in the reaction solution and other factors. These purification methods can also be combined.

The present inventors discovered that a simple substance consisting entirely of mannose units with a degree of polymerization of at least 3—preferably at least 4—exhibits a powerful lipid absorption inhibiting effect and sugar absorption inhibiting effect. They also discovered that a fraction of a sugar with a degree of polymerization of 3-10 and mannose units constituting at least 90% of the numerical content dramatically reduces liver lipids. Based on these results, it became clear that a mixture or simple substance of a sugar with a degree of polymerization of 3-10 and mannose units constituting at least 66% of the numerical content—preferably at least 90%, more preferably at least 95%, and most preferably consisting entirely of mannose units—is useful for efficiently reducing lipids in the liver by inhibiting the absorption of lipids and sugar.

The prevention or treatment of lifestyle-related diseases in the present application becomes possible by orally ingesting the pharmaceutical composition of the present application to suppress lipid absorption and sugar absorption. Since the quantities of lipids or sugar absorbed into the body can be suppressed regardless of the quantities of lipids or sugar of the meal ingested, it is possible to prevent lifestyle-related diseases caused by obesity without changing one's dietary preferences.

Liver lipid reduction in the present application refers to the reduction of triglycerides and total cholesterol accumulated in the liver as a result of the suppression of the quantities of lipids and/or sugar absorbed into the body. Being able to reduce liver lipids not only has a direct prophylactic effect on hyperlipidemia and hypercholesterolemia, but it also makes it possible to exhaustively prevent lifestyle-related diseases such as diabetes, arteriosclerosis, and liver failure.

The present inventors discovered that simple substances with degrees of polymerization of 4 or higher consisting entirely of mannose units also promote the growth of bifidobacteria. This result indicates that a mixture or simple substance of a sugar with a degree of polymerization of 3-10 and mannose units constituting at least 66% of the numerical content—preferably at least 90%, more preferably at least 95%, and most preferably consisting entirely of mannose units—is useful for preventing lifestyle-related diseases such as large intestine cancer by promoting the growth of bifidobacteria and thereby favorably maintaining the intestinal environment.

The pharmaceutical composition for preventing or treating lifestyle-related diseases of the present application can be formulated in any form such as a tablet, powder medicine, granules, capsule, lozenge, or syrup together with excipients and other additives. Examples of excipients and additives include solid substances such as lactose, sucrose, microcrystalline cellulose, corn starch, agar, pectin, stearic acid, magnesium stearate, lecithin, and sodium chloride or liquid substances such as glycerin, polyvinylpyrrolidone, olive oil, ethanol, benzyl alcohol, propylene glycol, and water. The quantity of the fraction of the sugar with a degree of polymerization of 3-10 and mannose units constituting at least 66% of the numerical content is 0.1-100 weight % of the total quantity of the pharmaceutical composition, preferably 1-100 weight %, and more preferably 5-95 weight %.

When orally administering the pharmaceutical composition of the present application to humans, the quantity of the fraction of the present application fluctuates depending on factors such as age, weight, sex, and administration method, but the daily intake for one adult male is preferably approximately 10-500 mg/kg of body weight and more preferably approximately 30-70 mg/kg of body weight, for example.

Examples of food products containing the sugar with a degree of polymerization of 3-10 and mannose units constituting at least 66% of the numerical content in the present application include liquid coffee, instant coffee, and coffee mix drinks. Examples of liquid coffee include products called coffee drinks or drinks containing coffee that are sealed in cans or so-called plastic bottle containers and sold, and an example of instant coffee is a drink called soluble powder coffee in which the water content is removed from an extract obtained by extracting roasted and ground coffee in hot water by means of a spray or freeze-drying method. An example of a coffee mix drink is a drink prepared by adding and mixing sugar or creaming powder into soluble powder coffee. The ratio of the sugar with a degree of polymerization of 3-10 and mannose units constituting at least 66% of the numerical content in these food products is 0.1-80 weight % of the total quantity of the food product, preferably 1-70 weight %, and more preferably 3-60 weight %.

industrial use, and this was concentrated to form 7 kg of a coffee extract residue (dry weight).

After this was pulverized to a particle size of approximately 1 mm, it was transferred to a 4 m thermal plug flow reactor. Water was then added, and this was heat treated after it was transformed into a slurry with a total solid concentration of approximately 14 weight %. This was pumped into a plug flow reactor with high-pressure steam at a rate corresponding to a retention time of 8 minutes, and it was kept at approximately 210° C. using an orifice with a diameter of 6.35 mm. The reaction was then stopped suddenly by pumping the solution out under atmospheric pressure. Next, 200 g of activated charcoal was added to 1 kg of a coffee extract containing mannooligosaccharides, and after this was heated to 60° C. and stirred for 1 hour, diatomaceous soil was added, stirred, and filtered. After the filtrate was successively passed through a column filled with a strong cation-exchange resin (Diaion SK-1B) and a column filled with a weak anion-exchange resin (Diaion SA-12A), it was freeze-dried in a vacuum to form 650 g of solid content containing only mannose and mannooligosaccharides.

High-purity fractions with various degrees of polymerization (called "DP" hereinafter) were obtained by column chromatography in which two types of ion-exchange resins (Diaion UBK-510L and UBK-530) were connected in series with a column having an inside diameter of 40 Φ and a length of 1500 mm.

In this operation, the column and the mobile phase were kept at 65° C. The flow rate was set to 20 ml/min, and the samples used for column chromatography were formed by dissolving 10 g of the solid content described above in 20 g of water. After a fraction primarily containing mannooligosaccharides with a specific DP was obtained, the operation in which the fraction was infused, back into the column was repeated to obtain high-purity fractions respectively containing at least 90% of DP2, DP3, DP4, and DP5 on their own. Fractions of DP6 and higher were obtained with a total of at least 90% of DP6-10. Here, DP3, for example, refers to a mannooligosaccharide consisting of only 3 mannose units. Each fraction was freeze-dried in a vacuum. The ingredients in the dried product of each fraction are shown in Table 1.

TABLE 1

| Each fraction group | Content of each fraction (%) | | | | | | | | |
|---|---|---|---|---|---|---|---|---|---|
| | DP2 | DP3 | DP4 | DP5 | DP6 | DP7 | DP8 | DP9 | DP10 |
| DP6 or higher | 0.0 | 0.0 | 0.0 | 0.4 | 12.6 | 26.0 | 27.0 | 13.7 | 20.3 |
| DP5 | 0.0 | 0.0 | 1.6 | 94.4 | 4.1 | 0.0 | 0.0 | 0.0 | 0.0 |
| DP4 | 0.0 | 1.5 | 96.9 | 1.6 | 0.0 | 0.0 | 0.0 | 0.0 | 0.0 |
| DP3 | 0.1 | 99.0 | 0.8 | 0.0 | 0.0 | 0.0 | 0.0 | 0.0 | 0.0 |
| DP2 | 98.5 | 1.5 | 0.0 | 0.0 | 0.0 | 0.0 | 0.0 | 0.0 | 0.0 |
| Mannooligosaccharides | 19.7 | 27.7 | 21.6 | 17.8 | 6.1 | 4.9 | 2.1 | 0.0 | 0.0 |

EMBODIMENTS

These embodiments are for the purpose of giving concrete descriptions of the modes for carrying out the present application, and they are not intended to limit the scope of the present application.

Embodiment 1

Mannooligosaccharide High-Purity Fractions

Ten kg of roasted and ground coffee obtained by conventional means was extracted with a percolation system for Embodiment 2

Inhibition of Lipid Absorption by the Administration of the Fractions Obtained in Embodiment 1

SD male Wistar rats were used in the experiment. Preliminary rearing was performed for 7 days, including a quarantine and acclimation period, and animals demonstrating no abnormalities in their body weight profiles or general conditions were divided into 6 groups with 10 animals per group and used in the experiment. The animals were reared in an environment in which the temperature, humidity, ventilation rate, and lighting hours were controlled. After 80 mg of cholic acid and 2 g of cholesterol oleate were added to 6 mL of corn oil, 6 mL of water for injection was added, and this was subjected to supersonic treatment for 10 minutes to form a suspension, which was used as a control solution. Experimental samples were prepared by adding unfractionated products and each fraction with DP2, DP3, DP4, DP5, and DP6 or higher obtained in Embodiment 1 to this control solution so that the concentration was 700 mg/2 mL of control solution per 1 kg of body weight. Each experimental sample was orally force-administered to unanesthetized animals using syringe barrels and feeding needles. Blood was collected from the tail veins of the animals without anesthesia before administration and 30, 60, 120, 180, 240, and 330 minutes after administration. The amount of triglycerides in serum was measured using a commercially available triglyceride measurement kit, and the total amount of lipids present during this time was calculated.

The results are shown in Table 2 and FIG. 1.

TABLE 2

| Fraction | Control solution | Unfractionated form | DP2 | DP3 | DP4 | DP5 | DP6 or higher |
|---|---|---|---|---|---|---|---|
| Triglycerides in blood (AUC) | 198.9 | 83.9 | 153.1 | 35.3 | 9.2 | 18.8 | 12.3 |

The blood triglyceride profiles tended to be lower in the groups treated with the unfractionated product and fractions than in the control group. The profiles in each group with DP3 or higher tended to be lower than in the unfractionated product group and the DP2 group. This result makes it clear that although the level of triglycerides in blood can be reduced by administering the unfractionated product or any of the fractions, an even better lipid absorption inhibitory action can be achieved by administering those with DP3 or higher in mixtures or as simple substances.

Embodiment 3

Preparation of High-DP Fractions, Medium-DP Fractions, and Low-DP Fractions

Ten g of the solid, content containing only mannose and mannooligosaccharides obtained in Embodiment 1 was dissolved in 20 g of water and fractionated using the same method as in Embodiment 1. However, the eluate was fractionated in quantities of 50 ml using a fraction collector, and fractions with eluate volumes of 1200-1450 were defined as high-DP fractions, fractions with 1450-1650 ml were defined as medium-DP fractions, and those with 1650-2100 ml were defined as low-DP fractions. Each fraction was freeze-dried in a vacuum and used in tests. The contents in the dried products are shown in Table 3.

TABLE 3

| Each fraction group | Content of each fraction (%) | | | | | | | | |
|---|---|---|---|---|---|---|---|---|---|
| | DP1 | DP2 | DP3 | DP4 | DP5 | DP6 | DP7 | DP8 | DP9 |
| Low-DP | 2.3 | 56.8 | 35.1 | 5.0 | 0.8 | 0.0 | 0.0 | 0.0 | 0.0 |
| Medium-DP | 0.0 | 0.4 | 25.8 | 40.0 | 21.9 | 7.9 | 4.0 | 0.0 | 0.0 |
| High-DP | 0.0 | 0.0 | 0.0 | 6.1 | 20.8 | 26.5 | 20.5 | 12.9 | 13.2 |
| Mannooligosaccharides | 0.0 | 19.7 | 27.7 | 21.6 | 17.8 | 6.1 | 4.9 | 2.1 | 0.0 |

Embodiment 4

Reduction of Liver Lipids by the Administration of the Fractions Obtained in Embodiment 3

Female ICR mice were used in the experiment. Preliminary rearing was performed for 7 days, including a quarantine and acclimation period, and animals demonstrating no abnormalities in their body weight profiles or general conditions were divided into 5 groups with 8 animals per group and used in the experiment. The animals were reared in an environment in which the temperature, humidity, ventilation rate, and lighting hours were controlled. The animals were allowed to freely consume feed prepared by mixing 1% of the unfractionated product and each of the low-DP, medium-DP, and high-DP fractions into high-fat feed containing 40% beef tallow as a base and feed containing no fractions (control feed) for 56 days. Once the administration period was complete, the livers of the animals were sampled, and after 4.5 mL of cold 0.1 MPBS was added to approximately 0.5 g of liver tissue and homogenized, it was centrifuged at 3000 rpm and the supernatant was collected. Using the supernatant as a sample, the quantity of lipids was measured with a commercially available triglyceride measurement kit.

Figure 2:
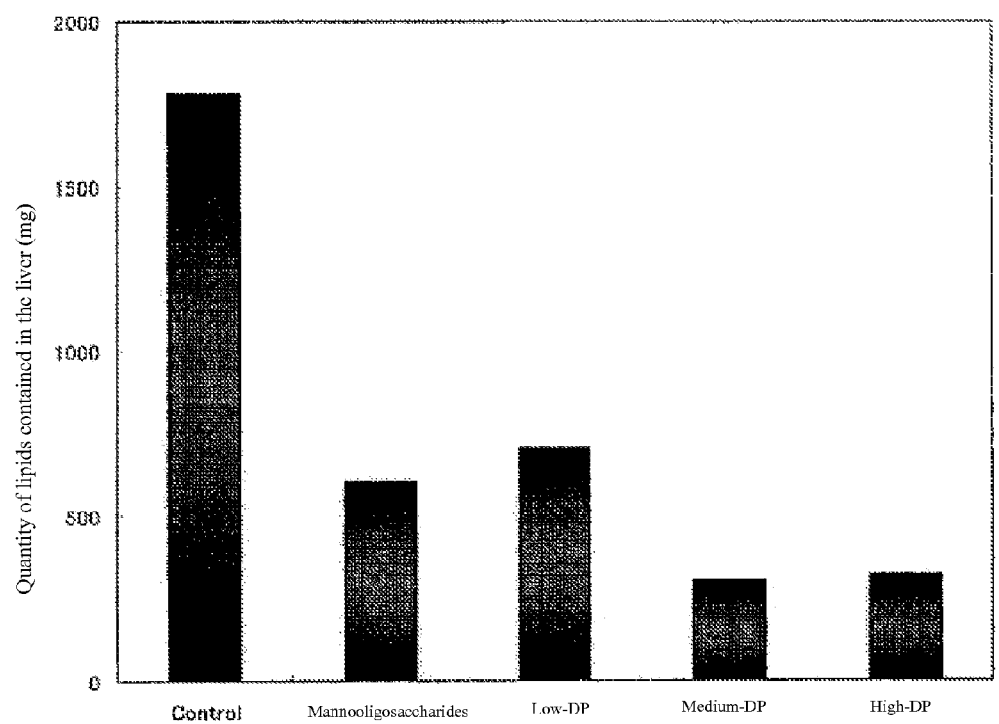
FIG. 2 shows the reduction in liver lipids resulting from the administration of fractions obtained in Embodiment 3.

The results are shown in Table 4 and FIG. 2.

TABLE 4

| Fraction | Control feed | Unfractionated form | Low DP | Medium DP | High DP |
|---|---|---|---|---|---|
| Liver lipids (mg) | 1783.6 | 601.0 | 702.7 | 302.0 | 317.1 |

The liver lipid levels were significantly lower in the groups treated with the unfractionated product and each fraction than in the control group. They were also significantly lower in the medium-DP fraction group and the high-DP fraction group than in the unfractionated product group and the low-DP fraction group. It became clear from this result that although liver lipids are reduced by the administration of any of the fractions, the liver lipid levels are reduced most by the administration of medium-DP fractions and high-DP fractions. This suggests that an even more significant liver lipid reducing action can be achieved by administering mixtures containing at least 90% of at least medium-DP fractions—in other words, DP3 or higher—for a long period of time.

Embodiment 5

Inhibition of Sugar Absorption by the Administration of the High-DP Fractions Obtained in Embodiment 3

Male [Wistar] rats were used. After preliminary rearing was performed for 7 days, including a quarantine and acclimation period, animals demonstrating no abnormalities in their body weight gains or general conditions were divided into 3 groups with 10 animals per group and used in the experiment. The animals were reared in an environment in which the temperature, humidity, ventilation rate, and lighting hours were controlled. Samples prepared by dissolving 12 g/kg of body weight, of starch in water were administered to the control group, and samples prepared by dissolving 12 g/kg of body weight of starch and 1.7 g/kg of body weight of the mannooligosaccharide unfractionated product in water were administered to the unfractionated group. Samples prepared by dissolving 12 g/kg of body weight of starch and 1.7 g/kg of body weight of the high-DP fractions obtained in Embodiment 3 in water were administered to the high-DP group. The samples were orally force-administered to the animals without anesthesia using syringe barrels and feeding needles. Blood was collected from the tail vein of each animal without anesthesia before administration and 15, 30, 60, 120, 180, and 240 minutes after administration. The blood sugar levels were measured using a commercially available kit, and the total blood sugar level present during this time was calculated.

Figure 3:
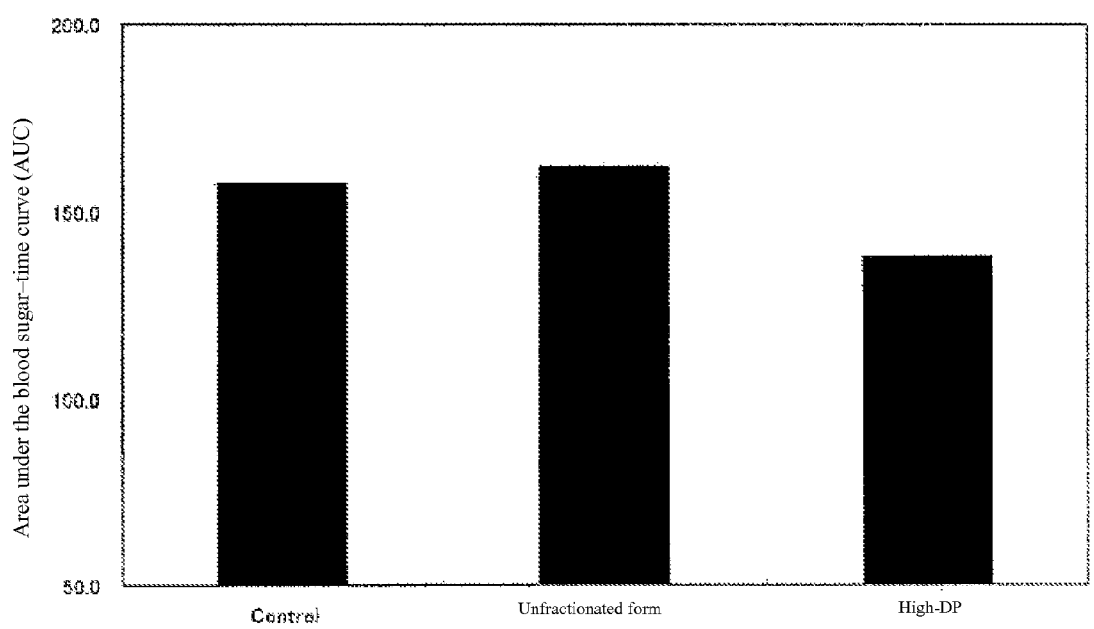
FIG. 3 shows the inhibition of sugar absorption resulting from the administration of fractions obtained in Embodiment 3.

The results are shown in Table 5 and FIG. 3.

TABLE 5

| Fraction | Control | Unfractionated form | High DP |
|---|---|---|---|
| Total blood sugar (AUC) | 157.9 | 161.8 | 137.9 |

The total blood sugar level tended to be lower in the high-DP group than in the control group and the unfractionated group. This result demonstrates that sugar absorption is inhibited by the administration of mixtures of DP3 or higher, which are the high-DP fractions.

Embodiment 6

Effects of the Fractions Obtained in Embodiment 3 on Intestinal Flora

Once the administration periods were complete in the control feed group and the high-DP fraction group in Embodiment 4, the entire cecal content was collected and then immediately placed on ice to measure the flora. This measurement was performed in accordance with the method of Mitsuoka ("The World of Intestinal Bacteria," edited by Chisoku Mitsuoka, published in 1984, Toji Shobo Shinsha). The sum of the total number of anaerobic bacteria (number of colonies on an EG culture medium or BL culture medium) and the total number of aerobic bacteria (number of colonies on a TS culture medium) was used as the total number of bacteria. Of these, the groups of bifidobacteria were identified by the shape of the colonies on the BL culture medium, Gram staining, and the cellular form and counted to find the number of bifidobacteria, and the ratio of bifidobacteria to the total number of bacteria was calculated. The results are shown in Table 6. It was confirmed that the ratio of bifidobacteria increases in the high-DP fraction group.

TABLE 6

| Control feed group | High-DP fraction group |
|---|---|
| 10.7% | 20.3% |

Embodiment 7

Tablet Preparation Method

After 20% lactose, 20% starch, and 6% microcrystalline cellulose were mixed with 50% fraction powder of DP6 or higher obtained in Embodiment 1, a hydroxypropyl cellulose 10% ethanol solution was added at a volume of 3%, and this was kneaded, granulated, and extruded using a screen with a diameter of 0.8 mm. After granules were prepared and dried, magnesium stearate was added at a volume of 1%, and a 300 mg tablet was prepared by compression molding. This tablet can be expected to have a prophylactic effect or a therapeutic effect on lifestyle-related diseases when taken at approximately 3 tablets per day.

Embodiment 8

Powdered Medicine Preparation Method

After 10% dextrin and water were added to 90% fraction powder with DP6 or higher obtained in Embodiment 1, a granulated product was obtained by mixing, heating, and granulating with a fluidized bed granulator. The obtained granulated product was packed directly or as a pulverized powder into sticks at a volume of 2 g per stick using a stick filler. This powdered medicine can be expected to have a prophylactic effect or a therapeutic effect on lifestyle-related diseases when taken at approximately one pouch per day.

Embodiment 9

Coffee Drink Preparation

After 3 g of the fraction powder with DP6 or higher obtained in Embodiment 1 and 0.17 g of concentrated coffee extract liquid (11 g of solid coffee content) and artificial sweetener were dissolved in 1000 ml of water and UHT-sterilized, the solution was placed in a plastic bottle. This coffee drink has a more full-bodied coffee flavor than ordinary coffee drinks. Moreover, it can be continuously ingested daily, and it can be expected to be useful in the prevention of lifestyle-related diseases.

The composition of the present application having the function of a prophylactic or therapeutic drug for lifestyle-related diseases can be used not only as a pharmaceutical, but also in a wide range of fields such as cosmetics, foods and drinks, and animal feeds, and it can be expected to have a prophylactic or therapeutic effect on lifestyle-related diseases caused by obesity.

The invention claimed is:

1. A method for treating lifestyle-related diseases, wherein an effective dose of a pharmaceutical composition is administered to a patient who is at risk of contracting or is suffering from a lifestyle-related disease in an amount effective to reduce liver lipids and/or reduce absorption of sugar in the patient when compared to an individual that is not administered the pharmaceutical composition, the pharmaceutical composition including an effective amount of an active ingredient comprising a sugar with a degree of polymerization of 5-10 and mannose units constituting at least 66% of the numerical content, wherein less than about 1% of the sugar has a degree of polymerization of less than 3, wherein the lifestyle-related disease is selected from the group consisting of obesity, metabolic syndrome, hyperlipidemia, diabetes, hypercholesterolemia, and liver failure, wherein the sugar is obtained by performing hydrolysis treatment on mannan and the mannan is obtained from coffee beans and/or a coffee extract residue.

2. The method according to claim 1, wherein mannose units constitute at least 90% of the numerical content.

3. The method according to claim 1, wherein said sugar has a degree of polymerization of 5-10 and consists entirely of mannose units.

4. The method according to claim 3, wherein said sugar is a β-1,4-mannooligosaccharide.

5. The method according to claim 1, wherein the active ingredient is provided in an amount effective to reduce lipid absorption.

6. The method according to claim 5, wherein said lifestyle-related disease is caused by increases in liver lipids.

7. The method according to claim 1, wherein the active ingredient is provided in an amount effective to reduce sugar absorption.

8. The method according to claim 7, wherein the active ingredient is provided in an amount effective to reduce liver lipids.

9. The method according to claim 1, wherein the sugar with a degree of polymerization of 5-10 is obtained by processing mannan contained in raw coffee beans, roasted coffee beans, or used coffee residues with one or more methods selected from the group consisting of acid hydrolysis, high-temperature thermal hydrolysis, oxygen hydrolysis, and microbial fermentation, followed by purification with a process selected from the group consisting of activated carbon treatment, absorbent resin treatment, ion-exchange resin treatment, and ion-exchange membrane treatment.

10. A method for treating lifestyle-related diseases, wherein an effective dose of a pharmaceutical composition is administered to a patient who is at risk of contracting or is suffering from a lifestyle-related disease in an amount effective to reduce liver lipids and/or reduce absorption of sugar in the patient when compared to an individual that is not administered the pharmaceutical composition, the pharmaceutical composition including an effective amount of an active ingredient comprising a sugar with a degree of polymerization of 5-10 and mannose units constituting at least 90% of the numerical content, wherein less than about 1% of the sugar has a degree of polymerization of less than 3, wherein the lifestyle-related disease is selected from the group consisting of obesity, metabolic syndrome, hyperlipidemia, diabetes, hypercholesterolemia, and liver failure, wherein the sugar is obtained by Performing hydrolysis treatment on mannan and the mannan is obtained from coffee beans and/or a coffee extract residue.

11. A method for reducing liver lipids and/or reducing absorption of sugar in a patient, wherein an effective dose of a pharmaceutical composition is administered to the patient in an amount effective to reduce liver lipids and/or reduce absorption of sugar in the patient when compared to an individual that is not administered the pharmaceutical composition, the pharmaceutical composition including an effective amount of an active ingredient comprising a sugar with a degree of polymerization of 5-10 and mannose units constituting at least 66% of the numerical content, wherein less than about 1% of the sugar has a degree of polymerization of less than 3, wherein the sugar is obtained by performing hydrolysis treatment on mannan and the mannan is obtained from coffee beans and/or a coffee extract residue.

12. The method according to claim 11, wherein mannose units constitute at least 90% of the numerical content.

13. The method according to claim 11, wherein said sugar has a degree of polymerization of 5-10 and consists entirely of mannose units.

14. The method according to claim 13, wherein said sugar is a β-1,4-mannooligosaccharide.

15. The method according to claim 11, wherein the active ingredient is provided in an amount effective to reduce lipid absorption.

16. The method according to claim 11, wherein the active ingredient is provided in an amount effective to reduce sugar absorption.

17. The method according to claim 16, wherein the active ingredient is provided in an amount effective to reduce liver lipids.

* * * * *